United States Patent
Schurr et al.

(10) Patent No.: US 11,484,190 B2
(45) Date of Patent: Nov. 1, 2022

(54) CAPSULE WITH BLOOD DETECTING SENSOR

(71) Applicant: Ovesco Endoscopy AG, Tübingen (DE)

(72) Inventors: Marc O. Schurr, Tübingen (DE); Sebastian Schostek, Tübingen (DE)

(73) Assignee: Ovesco Endoscopy AG

( * ) Notice: Subject to any disclaimer, the term of this patent is extended or adjusted under 35 U.S.C. 154(b) by 967 days.

(21) Appl. No.: 16/316,742

(22) PCT Filed: May 29, 2017

(86) PCT No.: PCT/EP2017/062920
§ 371 (c)(1),
(2) Date: Jan. 10, 2019

(87) PCT Pub. No.: WO2018/010885
PCT Pub. Date: Jan. 18, 2018

(65) Prior Publication Data
US 2020/0229687 A1 Jul. 23, 2020

(30) Foreign Application Priority Data
Jul. 12, 2016 (EP) .................................... 16179069

(51) Int. Cl.
*A61B 5/1455* (2006.01)
*A61B 1/04* (2006.01)
(Continued)

(52) U.S. Cl.
CPC ............ *A61B 1/041* (2013.01); *A61B 5/0075* (2013.01); *A61B 5/02042* (2013.01);
(Continued)

(58) Field of Classification Search
CPC ..... A61B 5/1455; A61B 5/041; A61B 5/0075; A61B 5/073
See application file for complete search history.

(56) References Cited

U.S. PATENT DOCUMENTS

| 8,911,368 B2 * | 12/2014 | Rabinovitz ............ A61B 5/073 600/309 |
| 2006/0231749 A1 | 10/2006 | Colvin et al. |
| 2014/0296666 A1 | 10/2014 | Rabinovitz et al. |

FOREIGN PATENT DOCUMENTS

| EP | 2057934 A1 | 5/2009 |
| JP | 2015509744 A | 4/2015 |

(Continued)

OTHER PUBLICATIONS

European Search Report for European Application No. 16 179 069.6, dated Jan. 18, 2017—8 pages.

(Continued)

*Primary Examiner* — Marjan Fardanesh
(74) *Attorney, Agent, or Firm* — RatnerPrestia

(57) ABSTRACT

A medical capsule is equipped with a sensor device having light emitting and light receiving elements. The sensor device can detect blood on the basis of light absorption properties of the blood. The capsule has a casing forming a recess or gap at its outer surface. The recess has a preselected width which represents a fixed measuring track between the light emitting and light receiving elements being arranged at opposing sides of the recess or gap when seen in its width direction. The medical capsule also has a shielding plate/layer/membrane arranged at least at or near the bottom of the recess or gap and extending along the width direction of the recess or gap preferably to exceed the recess at both sides into its width direction to prohibit emitted light from bypassing the recess via the casing material of the capsule.

12 Claims, 1 Drawing Sheet

(51) Int. Cl.
      *A61B 5/00*       (2006.01)
      *A61B 5/02*       (2006.01)
      *A61B 5/07*       (2006.01)

(52) U.S. Cl.
      CPC ........ *A61B 5/073* (2013.01); *A61B 2562/162* (2013.01); *A61B 2562/166* (2013.01)

(56) References Cited

FOREIGN PATENT DOCUMENTS

| WO | 0013003 A1 | 3/2000 |
|---|---|---|
| WO | 2013088444 A2 | 6/2013 |

OTHER PUBLICATIONS

International Search Report and Written Opinion for Application No. PCT/EP2017/062920, dated Sep. 13, 2017—8 pages.
Notification of Reasons for Rejection for Japanese Application No. 2019-501514, dated Mar. 10, 2021, with translation, 6 pages.

\* cited by examiner

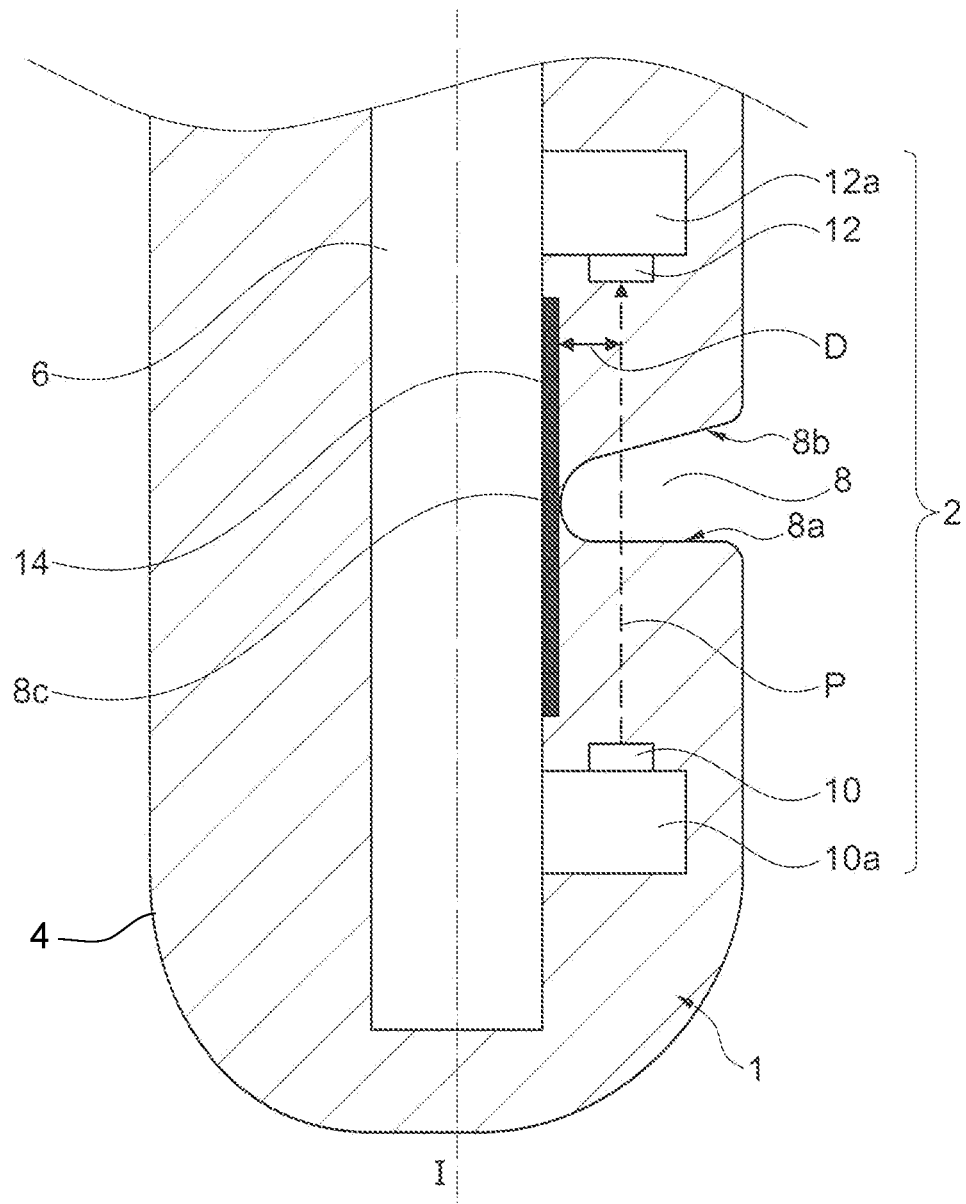

CAPSULE WITH BLOOD DETECTING SENSOR

RELATED APPLICATIONS

This application is the United States national phase entry of International Application No. PCT/EP2017/062920, filed May 29, 2017, which claims the benefit of priority of European Application No. EP 16179069.6, filed Jul. 12, 2016. The contents of International Application No. PCT/EP2017/062920 and European Application No. EP 16179069.6 are incorporated by reference herein in their entireties.

FIELD

The present invention relates to a capsule equipped with a sensor device being adapted to detect blood especially gastrointestinal bleedings.

BACKGROUND

Acute upper gastrointestinal bleedings from ulcers or esophago-gastric varices are life threatening medical conditions which require immediate endoscopic therapy. Despite successful endoscopic hemostasis, there is a significant risk of rebleeding often requiring close surveillance of these patients in the intensive care unit. Any time delay to recognize bleeding may lead to a high blood loss and increases the risk of death.

For example from the prior art document EP 2 057 934 A1 of the present inventor, the content of which is also made to the subject matter of the present invention, a telemetric real-time bleeding sensor is known which can help to indicate blood in the stomach. This known sensor is swallowed to detect active bleeding or is anchored endoscopically on/at the gastrointestinal wall close to the potential bleeding source/area. By telemetric communication with an extracorporeal receiver, information about the bleeding status is displayed.

In order to be able to safely detect the presence of blood the sensor being used in the above described capsule is adapted to measure characteristic optical properties of blood. More concrete, blood has the characteristic optical property of high absorption of violet light, while red light is comparatively well transmitted. This optical property of blood is used for the sensor.

At the minimum at about 41.5 nm (violet), transmission is up to three orders of magnitude lower than transmission at a wavelength of about 720 nm (red) depending on the optical density of the blood sample. According to these optical characteristics of blood, a quotient of the measured intensity of red light divided by the measured intensity of violet light is used as a single indicator value to predict the presence of blood. Thus the quotient increases with decreasing violet intensity indicating a higher concentration of blood.

The optical sensor according to the above-mentioned prior art document is a ratiometric intensity-based sensor. It is designed to be miniaturized for integration into a swallowable or implantable capsule. The aim is to compare the transmission of light at about 415 nm to the transmission of light at about 700, preferably 720 nm. For this purpose, the implant cast or housing provides at least one recess, through which light from two LED's of the respective wavelengths is transmitted sequentially. The recess is dimensioned to allow fluids to flow into the optical pathway of the sensor crossing the recess substantially orthogonal thereto into the width direction of the recess. The remaining intensity if the light after its travel through the recess (in the width direction thereof) is measured by a photo transistor being arranged opposite to the LED's on the other side of the recess. This allows the swallowed/implanted capsule to calculate the ratio between the received violet and the red light. Since LED's are known to have relevant tolerances, due to manufacturing and temperature dependency, each individual sensor is/can be calibrated in post-processing to compensate for these effects.

Despite of the above technical properties of the well-known sensor device being used in capsules of this kind and the provision of the calibrating mode before taking the sensor device into use it turned out that the measuring results sometimes deviate from each other although the outer boundary conditions (presence of a predetermined amount of blood in a test sample) has not been changed.

Accordingly, such kind of deviations generally make the reliability of the sensor device and the capsule having such a sensor device inappropriate for its use in the intensive care unit. For the above reason, it is an objective object of the present invention to improve the accuracy of measurement for capsules equipped with a sensor device being adapted to detect blood to allow reproducibility of a plurality of measuring results for same (non-changed) boundary conditions.

The applicant has carried out a plurality of tests and investigations and realised that a part of the light (violet and/or red) emitted by the LED's on one side of the recess is not transmitted through the fluid within the recess to the light receiving sensor on the other side of the recess (direct light path between LED's and sensor) but is fed through the capsule casing bypassing the recess and the fluid collected within the recess. The amount/percentage of light being fed by/through the capsule casing does not depend on the absorption properties of the fluid within the recess but depends on the light feeding property (translucence) of the material of the capsule casing which is substantially constant and to the surface quality of the capsule casing facing the recess. Accordingly, in case the casing surface is covered by, for example, a plaque material generated by the fluid within the recess, the amount/percentage of light entering the capsule material might be reduced wherein in case the casing surface is not covered by, for example, a plaque material, the amount/percentage of light entering the capsule material might be increased.

In order to avoid such kind of noise the present invention provides according to a first aspect a capsule being equipped with a sensor device which is adapted to detect blood especially gastrointestinal bleeding, wherein the capsule/the casing of the capsule is provided with a shielding plate/layer/membrane being arranged at least at/near the bottom of the recess and extending along the width of the recess preferably to protrude/exceed the recess on its both sides into its width direction.

According to a second advantageous aspect of the present invention the size/dimension of the shielding plate/layer/membrane may be adjusted such that it fits between the light emitting (LED's) and the light receiving element (light sensor) in the width direction of the recess.

According to another advantageous aspect of the present invention the shielding plate/layer/membrane may be embedded and/or moulded within the casing material (preferably made of resin). Preferably, the shielding plate/layer/membrane represents the bottom of the recess, which means it is exposed to the free surroundings at the bottom of the recess to provide an interruption/block/wall for stopping/prohibiting the transmission of light from the light emitting member to the light receiving member through the material of the capsule casing. It shall be noted here, that "freely exposed" does not necessarily mean that the plate material having the shielding characteristic (for example copper or the like) is freely exposed. This would be only one option. Another option would be to cover the plate material having the shielding characteristic with a (very thin) layer or film made of biocompatible material, wherein the thickness of such a film is selected/adjusted such that its light-transmission-capabilities are negligible.

According to another advantageous aspect of the present invention the shielding plate/layer/membrane may be a member separate/different to a circuit board accommodated within the capsule wherein the light emitting and light receiving members may be mounted on that circuit board.

According to another advantageous aspect of the present invention the shielding plate/layer/membrane may be arranged in a parallel distance to a direct light path between the light emitting and light receiving members According to another advantageous aspect of the present invention the shielding plate/layer/membrane may be mounted on the circuit board preferably on its outer surface being directed to the recess.

BRIEF DESCRIPTION OF THE DRAWING FIGURE

In the following, the present invention will be described on the basis of a preferred embodiment by reference of the enclosed FIGURE.

The enclosed FIGURE shows a front/rear part of a medical capsule for detecting the presence of blood by using a blood sensor/detecting device of well-known design and function.

DETAILED DESCRIPTION

According to the enclosed FIGURE, the inventive capsule 1 equipped with a sensor device 2 being adapted to detect blood especially gastrointestinal bleedings comprises a capsule casing 4 having a substantially cylindrical outer shape with rounded end portions and being made preferably of a resign material generally having light transmitting/light permeable properties. Within the capsule 1 at least one circuit board 6 is accommodated in a fluid-tight manner (moulded-in) at which a plurality of electronic facilities, representing the standard features of well-known medical capsules of this kind, are mounted like a data memory and/or data transmission member (memory chip, Blue Tooth, IR-transceiver), a calculator (CPU), light emitting and receiving members etc., being not shown in the FIGURE. Furthermore, the capsule 1 contains an energy source, for example, a battery (not shown).

The casing 4 of the capsule 1 is provided with a gap or recess 8 being orientated substantially, rectangular to the longitudinal axis A of the cylindrical capsule 1 such that its recess width extends in the longitudinal direction of the capsule. On one side 8a of the recess 8, when seen in the width direction thereof, a light emitting element/member 10 (for example, one or two LED's) is provided and oriented such that it admits light in violet and visual red range (at about 415 nm and at about 720 nm) through the recess 8 along the longitudinal direction of the capsule which light is detected by a light receiving element/member 12 (for example a light-sensitive sensor) which is located on the other side 8b of the recess 8, when seen in the width direction thereof opposite to the light emitting element/member 10. Accordingly, between the light emitting member 10 and light receiving member 12 a direct light transmission path P is generated having a predetermined/fixed path length and passing the recess 8 in its width direction.

At a bottom 8c of the recess 8, a shielding plate/layer/membrane 14 is provided within the capsule 1 having the property to block (substantially fully reflect or substantially fully absorb) at least the violet and red light being emitted by the light emitting element. More concrete, the shielding plate/layer/membrane is located within the capsule 1 in an area between the light emitting 10 and light receiving member 12 (just) below the recess 8. Preferably, the shielding plate/layer/membrane 14 represents/provides in a middle portion of it (at least partly) the bottom 8c of the recess 8 wherein in that portion the membrane 14 is freely exposed to the inner space (surroundings) of the recess 8. Finally, the shielding plate/layer/membrane 14 is orientated substantially parallel to the direct light transmission path P between the light emitting 10 and receiving members 12.

To achieve a parallel distance D between the shielding plate/layer/membrane 14 and the direct light transmission path/track P the light emitting 10 and light receiving members 12 are located on sockets 10a, 12a having a pre-selected height and being mounted on the circuit board 6. The parallel distance D is also pre-selected such that the direct light transmission path P (which corresponds to the measuring track) is located at about the middle height of the recess 8. Furthermore, it shall be noted that, in the present preferred embodiment of the invention, the recess 8 does not have a rectangular shape in its cross section but substantially trapezoid such that the recess width continuously narrows in the direction to the recess bottom 8c.

As can be also seen from the enclosed FIGURE, the shielding plate/layer/membrane 14 is a member being separate from the circuit board 6 but which may be mounted on the circuit board 8, for example by gluing. Preferably, it is embedded within the resign material of the capsule casing 4 wherein that portion of the shielding plate/layer/membrane 14 representing/providing the bottom 8c of the recess 8 is kept non-covered by the resin.

The function of the shielding plate/layer/membrane 14 can described as follows:

The shielding plate/layer/membrane 14 extends beyond the recess 8 at its both sides in the width direction thereof. Furthermore, at least at one (middle) portion of the shielding plate/layer/membrane 14, it is freely exposed to the internal space/gap within the recess 8. Accordingly, in case the light emitting member (LED's) 10 starts emitting (violet and/or red) light into the recess 8, at least a part/amount of the emitted light will most probably also enter the capsule material having some light transmission characteristic. However, because of the provision of the shielding plate/layer/membrane 14 as described above, the already entered light will be blocked at least at that (middle) portion of the membrane 14 being freely exposed to the internal space of the recess 8 from further traveling within the casing material parallel to the direct light transmission path P. In addition, because the shielding plate/layer/membrane 14 is provided between the light emitting and receiving elements 10, 12, wherein it exceeds both sides 8a, 8b of the recess 8 in its width direction the already entered light is prohibited from bypassing/surrounding the shielding plate/layer/membrane 14 at its side being averted from the recess 8 (back-side with respect to the recess 8)

The shielding plate/layer/membrane 14 can be made, for example, of a metal or aluminium sheet extending parallel (or vertical) to the direct light transmission path/track P as defined above to provide an entering and/or travelling block/wall for light waves especially violet and red light.

To summarise the subject matter of the present invention a medical capsule is disclosed herewith being equipped with a sensor device 2 comprising light emitting and light receiving elements 10, 12. The sensor device 2 is adapted to detect blood especially gastrointestinal bleeding on the basis of light absorption properties of the blood, wherein the capsule 1 is provided with a casing 4 forming a recess or gap 8 at its outer surface. The recess 8 has a pre-selected width which represents a fixed measuring track between the light emitting and light receiving elements 10, 12 being arranged at opposing sides 8*a*, 8*b* of the recess or gap 8 when seen in its width direction. The medical capsule 1 is provided with a shielding plate/layer/membrane 14 being arranged at least at or near the bottom 8*c* of the recess or gap 8 and extending along the width direction of the recess or gap 8 preferably to exceed the recess 8 at its both sides 8*a*, 8*b* into its width direction to prohibit emitted light from bypassing the recess 8 via the casing material of the capsule 1.

The invention claimed is:

1. A medical capsule being equipped with a sensor device comprising a light emitting element and a light receiving element, the sensor device adapted to detect blood on the basis of light absorption properties of the blood, wherein the medical capsule is provided with a casing forming a recess or gap at an outer surface of the casing having a recess width which represents a fixed measuring track between the light emitting element and the light receiving element being arranged at opposing sides of the recess or gap when seen in a width direction, wherein the recess or gap comprises a recess bottom, wherein the medical capsule is provided with a shielding plate or layer or membrane being arranged at least at or near a bottom of the recess or gap and extending along the width direction of the recess or gap to exceed the recess or gap at the opposing sides into its width direction, and wherein the shielding plate or layer or membrane comprises at least one middle portion being freely exposed to the inner space of the recess at the recess bottom.

2. The medical capsule according to claim 1, wherein the size or dimension of the shielding plate or layer or membrane is adjusted such that it that the plate or layer or membrane fits between the light emitting element and the light receiving element in the width direction of the recess or gap.

3. The medical capsule according to claim 1, wherein the shielding plate or layer or membrane is embedded or molded in the casing.

4. The medical capsule according to claim 3, wherein the shielding plate or layer or membrane is configured to provide an interruption or block or wall for stopping or prohibiting transmission of light from the light emitting element to the light receiving element through a material of the medical capsule casing.

5. The medical capsule according to claim 4, wherein the shielding plate or layer or membrane is covered by a film of biocompatible material.

6. The medical capsule according to claim 1, wherein the shielding plate or layer or membrane is a member being separate from a circuit board accommodated within the medical capsule or casing wherein the light emitting element and the light receiving element are mounted on the circuit board via sockets.

7. The medical capsule according to claim 1, wherein the shielding plate or layer or membrane is arranged in a parallel distance to a direct light path between the light emitting element and the light receiving element.

8. The medical capsule according to claim 6, wherein the shielding plate or layer or membrane is mounted on the circuit board on an outer side of the circuit board facing the recess or gap.

9. The medical capsule according to claim 1, wherein the shielding plate or layer or membrane is made from metal or metal alloy.

10. The medical capsule according to claim 1, wherein the bottom and the opposing sides of the recess or gap are oriented non-parallel to each other.

11. The medical capsule according to claim 1, wherein the recess or gap has a trapezoid shape in a cross-sectional view.

12. A medical capsule being equipped with a sensor device comprising light emitting and light receiving elements, the sensor device is adapted to detect blood especially gastrointestinal bleeding on the basis of light absorption properties of the blood, wherein the medical capsule is provided with a casing forming a recess or gap at an outer surface of the casing having a recess width which represents a fixed measuring track between the light emitting and light receiving elements being arranged at opposing sides of the recess or gap when seen in its width direction, wherein the medical capsule is provided with a shielding plate or layer or membrane being arranged at least at or near the bottom of the recess or gap and extending along the width direction of the recess or gap preferably to exceed the recess or gap at its both sides into its width direction, wherein the recess or gap has a trapezoid shape in a cross-sectional view.

\* \* \* \* \*